United States Patent
Tomita et al.

(10) Patent No.: US 6,767,209 B1
(45) Date of Patent: Jul. 27, 2004

(54) INTERDENTAL BRUSH AND PRODUCTION METHOD THEREFOR

(75) Inventors: Yoshikazu Tomita, Takahama (JP); Fujio Ito, Takahama (JP); Naoki Tsurukawa, Shijonawate (JP); Hitoshi Matsumoto, Suita (JP)

(73) Assignees: Sunstar Inc., Takatsuki (JP); Uni-Sunstar B.V., Amsterdam (NL)

( * ) Notice: Subject to any disclaimer, the term of this patent is extended or adjusted under 35 U.S.C. 154(b) by 0 days.

(21) Appl. No.: 09/856,167

(22) PCT Filed: Dec. 2, 1999

(86) PCT No.: PCT/JP99/06787

§ 371 (c)(1),
(2), (4) Date: Aug. 3, 2001

(87) PCT Pub. No.: WO00/33761

PCT Pub. Date: Jun. 15, 2000

(30) Foreign Application Priority Data

Dec. 4, 1998 (JP) .......................... 10-346130

(51) Int. Cl.[7] .............................. A61C 15/00
(52) U.S. Cl. ...................... 433/216; 132/329
(58) Field of Search ................ 433/216, 141, 433/142; 132/321, 329, 308; 15/167.1

(56) References Cited

U.S. PATENT DOCUMENTS

| | | | | |
|---|---|---|---|---|
| 3,295,156 A | * | 1/1967 | Brant | 15/167.1 |
| 5,775,346 A | * | 7/1998 | Szyszkowski | 132/329 |
| 6,220,980 B1 | * | 4/2001 | Adler | 473/613 |
| 6,253,404 B1 | * | 7/2001 | Boland et al. | 15/22.1 |

FOREIGN PATENT DOCUMENTS

| | | |
|---|---|---|
| JP | 61-37153 | 2/1986 |
| JP | 3-22723 | 3/1991 |
| JP | 9-168552 | 6/1997 |

* cited by examiner

Primary Examiner—Kevin Shaver
Assistant Examiner—Melba Bumgarner
(74) Attorney, Agent, or Firm—Armstrong, Kratz, Quintos, Hanson & Brooks, LLP

(57) ABSTRACT

Relates to an interdental cleaning tool provided on the peripheral surface of a shaft member 1 with one or a plurality of projections 2, the projections being pinnulate elements or cirrate elements, and shaft member 1 and projections 2 being integrally molded from synthetic resin, whereby there may be afforded a soft touch against the tissues of the oral cavity during use, deviation in extraction force of the pinnulate members and cirrate members may be prevented, and production costs may be reduced.

17 Claims, 19 Drawing Sheets

(a)

(b)

(a)

(b)

(c)

INTERDENTAL BRUSH AND PRODUCTION METHOD THEREFOR

BACKGROUND OF THE INVENTION

1. Field of the Invention

The present invention relates to an interdental cleaning tool for insertion between adjacent teeth to effect cleaning of the interdental gap, and to a method for the manufacture thereof.

2. Description of the Related Art

An interdental cleaning tool for insertion between adjacent teeth to effect cleaning of the interdental gap is fabricated by arranging a plurality of cirrate members fabricated from synthetic resin along a deflected piece produced by deflection of a single strand of wire into a "U" shape in the longitudinal central portion of, grasping the deflected piece at a first end and a second end thereof and twisting the deflected piece so that the cirrate members become embedded therein, and then severing the ends of the cirrate members to produce uniform cirrate member length, the article so fabricated being attached via one end of the wire to a handle of predetermined length fabricated from synthetic resin.

Apropos, in the interdental cleaning tools available commercially, cirrate members fabricated from synthetic resin are embedded in wire, and as the wire on occasion flexes during use, and as the cirrate members are moreover embedded in this wire by means of twisting, there may occur deviation in the anchoring force of the cirrate members to the wire, namely, in the extraction force of the cirrate members. Further, where an interdental cleaning tool is constructed using wire, there is required a process wherein the wire is deflected into a "U" shape, the cirrate members are arranged along the deflected piece, and the deflected piece is twisted so that the cirrate members become embedded therein, and it is further necessary to attach the wire to a handle of predetermined length, resulting in the problem of complexity of process and high cost. Further, the use of exposed wire creates the problem of a lack of a soft sensation against the tissues of the oral cavity.

There has been proposed previously an interdental cleaning tool that does not employ wire, being fabricated in its entirety from synthetic resin; however, this has been proposed merely in conceptual terms, the particulars thereof having yet to be suggested, with such a product remaining to be commercially developed.

With the foregoing in view, it is an object of the present invention to provide a process for the manufacture of an interdental cleaning tool wherein a shaft member and projections composed of pinnulate members and/or cirrate members are integrally molded from synthetic resin, thereby affording a soft sensation against the tissues of the oral cavity and eliminating any deviation in extraction force of the pinnulate members and cirrate members.

SUMMARY OF THE INVENTION

The interdental cleaning tool pertaining to a first invention is an interdental cleaning tool having one or a plurality of projections on the peripheral face of a shaft member, wherein the projections are pinnulate members and/or cirrate members, the shaft member and projections being integrally molded from synthetic resin.

According to the first invention, projections and a shaft member for insertion into gaps between adjacent teeth are integrally molded from synthetic resin, affording a soft sensation against the tissues of the oral cavity during use. Further, as the synthetic resin projections are integrally molded with shaft member, variation in projection extraction force is eliminated. Moreover, as the projections and shaft member constitute an integrally molded structure, manufacture involves a fewer number of manufacturing steps than does a corresponding product using wire, thus affording reduced cost.

Where the projection is a pinnulate member, cleaning performance by an individual projection is enhanced and projections are rendered highly durable.

According to the interdental cleaning tool pertaining to a second invention, projections are molded using a mold provided with cavities for forming projections, situated on parting faces thereof that intersect the axis of the shaft member or on parting faces thereof that are codirectional with the axis.

According to the second invention, a structure is possible wherein a plurality of projections are arranged codirectional with the circumference and axis of the shaft member, affording enhanced cleaning performance. The use of a split mold facilitates intricate machining of mold cavities.

According to the interdental cleaning tool pertaining to a third invention, projection size, namely pinnulate member thickness or cirrate member diameter, is 0.2 mm or smaller.

According to the third invention, maximum thickness for a pinnulate member or diameter for a cirrate member participating in interdental cleaning is 0.2 mm or smaller, whereby the pinnulate member or cirrate member is rendered flexible so as to give a pleasant sensation during use. Where pinnulate member maximum thickness or cirrate member diameter exceeds 0.2 mm, pinnulate members or cirrate members will lack flexibility, resulting in an unpleasant sensation during use.

According to the interdental cleaning tool pertaining to a fourth invention, projection length is 0.5 mm or greater.

According to the fourth invention, projections are 0.5 mm or greater in length, affording adequately enhanced cleaning performance. Where projections is shorter than 0.5 mm, the excessively short length of the projections, which participate in interdental cleaning, results in diminished cleaning performance.

The interdental cleaning tool pertaining to a fifth invention is provided with a plurality of projections, with pinnulate member density centered about the shaft member being at least 3 per 360° and cirrate member density in the axial direction of the shaft member being at least 8 per 1 mm of length.

According to the fifth invention, pinnulate member density centered about the shaft member is at least 3 per 360° and cirrate member density in the axial direction of the shaft member is at least 8 per 1 mm, thereby affording sufficiently good cleaning performance. Where pinnulate member density is less than 3 per 360° or cirrate member density is less than 8 per 1 mm, the resulting inadequate pinnulate member/cirrate member density will result in diminished cleaning performance.

According to the interdental cleaning tool pertaining to a sixth invention, a projection comprises a projection proper connecting to the shaft member and a branch member(s) integrally formed therewith and extending in a direction that intersects the axis of the projection proper.

According to the sixth invention, projections proper and branch members participate in interdental cleaning, increasing the number of points of contact with the tooth, thereby affording further enhanced cleaning performance.

According to the interdental cleaning tool pertaining to a seventh invention, the shaft member has a core element consisting of a material having a flexural modulus higher than the flexural modulus of the aforementioned synthetic resin, produced by insert molding or two-color molding. In the seventh invention, "core element consisting of a material having a flexural modulus higher than the flexural modulus of the aforementioned synthetic resin" will naturally include metal materials, and will include synthetic resin materials as well. Insert molding refers to a process wherein the core element is vised in a mold and a synthetic resin material then flowed into the mold; two-color molding refers to a process wherein the core element is formed first, followed by molding of other portions, including projections.

According to the seventh invention, projections which participate in interdental cleaning are endowed with good flexibility, excessive flexion of the shaft member is prevented, and shaft member strength is increased.

According to the interdental cleaning tool pertaining to an eighth invention, the material for the core element of the shaft member is synthetic resin having a flexural modulus higher than the flexural modulus of the synthetic resin used for projections.

According to the eighth invention, projections which participate in interdental cleaning are endowed with good flexibility, excessive flexion of the shaft member is prevented, and shaft member strength is increased.

According to the interdental cleaning tool pertaining to an ninth invention, the material for the core element of the shaft member is metal.

According to the ninth invention, there is no a twisting process, as with interdental cleaning tools using wire, and thus the core element may be composed of a highly rigid material such as piano wire, precluding bending of the shaft member. That is, wire material that will be subjected to a twisting process must have appreciable elongation, which precludes the use of highly rigid wire materials; here, the fact that the core element is simply subjected to insert molding means that a highly rigid material can be used.

The use of highly rigid metal also allows the diameter of the inserted core element to be thinner. By using a shape memory alloy (e.g. , Ni—Ti alloy, etc.) an interdental cleaning tool having become bent through use may be restored by immersing it in hot water.

According to the interdental cleaning tool pertaining to a tenth invention, the shaft member is molded from a synthetic resin having a flexural modulus higher than the flexural modulus of the synthetic resin used for the projections, and is molded integrally with the projections.

According to the tenth invention, the shaft member and projections can be integrally molded using within the mold one synthetic resin for the projections and another synthetic resin for the shaft member, thereby affording pliable projections as well as increased strength of the shaft member and affording a pleasant sensation during cleaning between the teeth.

According to the interdental cleaning tool pertaining to an eleventh invention, the shaft member and projections are injection molded from thermoplastic resin.

According to the eleventh invention, a finished interdental cleaning tool can be molded easily by melting thermoplastic resin at a suitable temperature and flowing the melt into a mold. The product will have softer contact against oral cavity tissues than will an interdental cleaning tool having synthetic resin cirrate elements embedded in wire, as in the conventional art example.

According to the interdental cleaning tool pertaining to a twelfth invention, the shaft member and the projections are injection molded from a thermoplastic elastomer.

According to the twelfth invention, the exceptional recovery of the thermoplastic elastomer prevents permanent bending of the shaft member, and the exceptional elasticity affords softer contact against oral cavity tissues.

According to the interdental cleaning tool pertaining to a thirteenth invention, the shaft member and projections are injection molded from a thermoplastic resin or thermoplastic elastomer having flexural modulus of 6000 kgf/cm$^2$ or above and a melt flow index of 8 g/10 min or above.

According to the thirteenth invention, the shaft member and projections resist bending owing to a flexural modulus of 6000 kgf/cm$^2$ or above and are rendered more highly durable. A melt flow index of 8 g/10 m in or above gives synthetic resin good flow when filling the mold, eliminating short shot in the cavities and giving a good molded shape. Where flexural modulus is below 6000 kgf/cm$^2$, the shaft will not insert well between teeth owing to inadequate strength. Where melt flow index is below 8 g/10 min, synthetic resin will have poor flow into the mold, making it difficult to produce projections of the desired length. A higher melt flow index is desirable, with 15 g/10 min or above being preferred, and 25 g/10 min or above being especially preferred.

According to the manufacturing method pertaining to a fourteenth invention, an interdental cleaning tool is manufactured using an injection mold divided into two sections along the axis of the shaft member.

According to the fourteenth invention, an interdental cleaning tool whose shaft member is provided with a plurality of projections may be molded using a mold having a simple construction.

According to the manufacturing method pertaining to a fifteenth invention, an interdental cleaning tool is manufactured using an injection mold split into three or more sections along the axis of the shaft member.

According to the fifteenth invention, the number and density of projections of an interdental cleaning tool whose shaft member is provided with a plurality of projections may be increased.

According to the manufacturing method pertaining to a sixteenth invention, an interdental cleaning tool is manufactured using a mold having a parting section in a mold section for molding projections. In the sixteenth invention, "parting section" refers to both mating portions for opening the mold and mating portions of the split mold not used for opening the mold.

According to the sixteenth invention, as a mold section is filled with synthetic resin, gas present in the mold section can escape to the outside through gaps in the parting section, allowing the synthetic resin to migrate up to the end of the mold section without the need to provide a special gas vent opening, thereby giving projections of desired length.

According to the manufacturing method pertaining to a seventeenth invention, an interdental cleaning tool is manufactured using a split mold having cavities for molding projections situated on a parting face thereof that intersects the axis of the shaft member.

According to the seventeenth invention, intricate machining of a plurality of cavities on parting faces of a split mold may be accomplished readily, whereby it is a simple matter to create a split mold for providing a plurality of projections along the circumference of the shaft member so that manufacturing costs for the interdental cleaning tool may be reduced. Further, gas present in a cavity can be vented through a gap between the parting faces, allowing the synthetic resin to migrate up to the end of the cavity without the need to provide a special gas vent opening. Cavities may be deliberately placed under negative pressure for molding.

According to the manufacturing method pertaining to an eighteenth invention, the split mold has thickness of from 0.1 to 2 mm in a direction intersecting the parting faces thereof.

According to the eighteenth invention, spacing between projections in the direction of the axis of the shaft member is small, viz., 0.1 to 2 mm, so that it is a simple matter to increase the number and density of projections arranged over the entire lengthwise extension of the shaft member.

According to the manufacturing method pertaining to a nineteenth invention, an interdental cleaning tool is manufactured using a mold split into three or more sections along the axis of the shaft member, the parting faces thereof being provided with cavities for molding projections.

According to the nineteenth invention, it is a simple matter to form cavities for a plurality of projections on the parting faces of a mold split into three or more sections, whereby an interdental cleaning tool having a plurality of projections arranged codirectional with the axis and circumference of the shaft member can be manufactured at reduced cost.

DESCRIPTION OF THE PREFERRED EMBODIMENTS

The embodiments of the invention are described hereinbelow with reference to the accompanying drawings.

Figure 1:
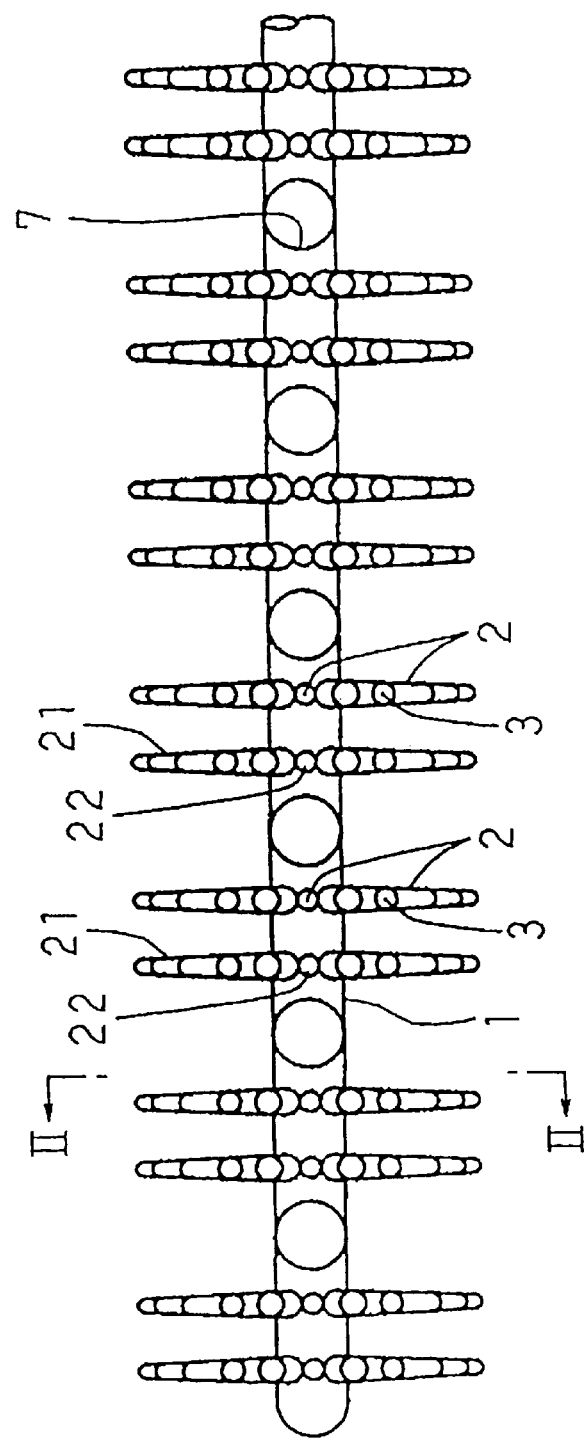
FIG. 1 is a front view depicting principal elements of an embodiment of the interdental cleaning tool pertaining to the invention.
Figure 2:
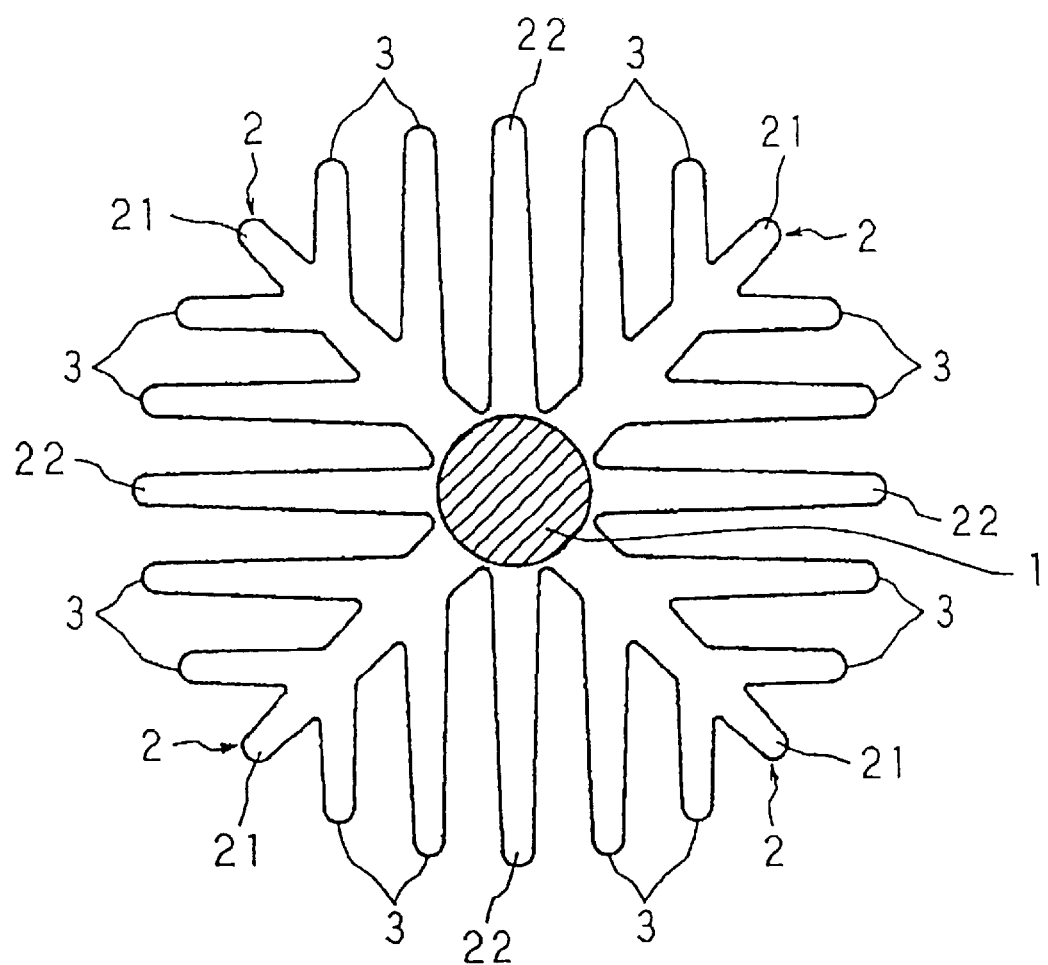
FIG. 2 is an enlarged section along line II—II in FIG. 1.
Figure 3:
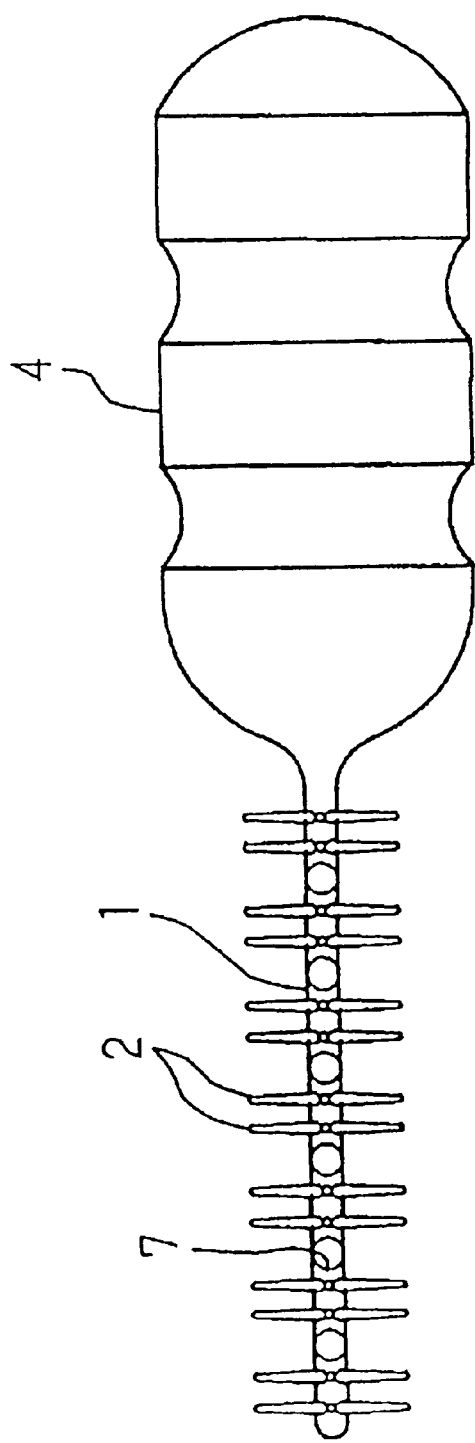
FIG. 3 is a front view of the interdental cleaning tool of the invention in its entirety.
Figure 4:
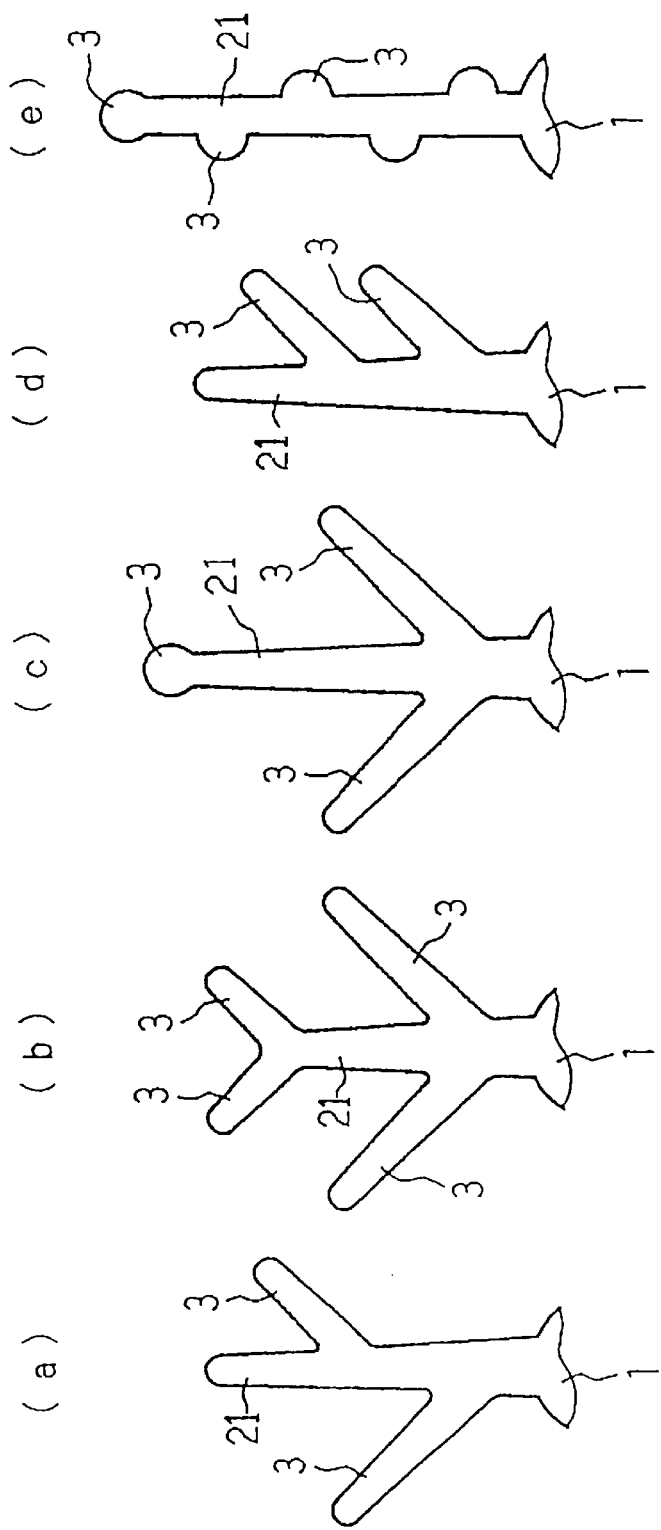
FIG. 4 gives partial side views of other embodiments of the branch element of the interdental cleaning tool of the invention.

FIG. 1 is a front view depicting principal elements of an embodiment of the interdental cleaning tool pertaining to the invention; FIG. 2 is an enlarged section along line II—II in FIG. 1; and FIG. 3 is a front view of the entirety.

The interdental cleaning tool comprises a plurality of cirrate projections 2 . . . arranged at desired intervals on the peripheral surface of a shaft member 1 codirectional with the circumference and axis thereof, and formed integrally therewith from molten synthetic resin; and a handle 4 of predetermined length integrally formed with the basal portion of the shaft member 1.

Shaft member 1 has the same contour, for example, a diameter of 0.5 mm, from the basal end to the distal end thereof, but may be designed to constrict in diameter going from the basal end to the distal end thereof.

The cirrate elements, namely, projections 2 . . . each comprise, for example, four projections proper 21 . . . extending radially at a phase difference of about 90°, and projections proper 22 . . . situated between these projections proper 21 . . . extending radially at a phase difference of about 45° with respect thereto; these projections proper 21 . . . , 22 . . . are provided integrally at desired intervals along the axis of shaft member 1, as shown in FIG. 1.

Projections 2 . . . have a circular cross section, the diameter thereof being 0.2 mm or less, and preferably 0.05 to 0.15 mm. Projections 2 . . . are 0.5 mm or greater in length. Density of projections 2 . . . is at least at least 8 per 1 mm of length in the direction of the axis of shaft member 1, with the intervals between projections 2 . . . along the shaft member axis being 0.1 to 2 mm.

Projections proper 21 . . . comprise at least one, and preferably a plurality of, branch elements 3 formed integrally therewith and branching out from projections proper 21 . . . in an intersecting arrangement therewith, whereby the projections proper 21 are pinnate.

As shown in FIG. 2, branch elements 3 ... are situated at two median locations along the lengthwise extension of projections proper 21 ... in sets of four extending from the two sides of each projection proper 21 at angles of about 45° within the same plane as projections proper 21 ..., 22 ... Branch elements 3 ... have a circular cross section, the diameter thereof being about equal to that of projections 2 ....

FIGS. 4(a)–(e) are partial side views of other embodiments of branch elements.

(a) shows projection proper 21 ... provided with one branch element 3 extending from each side thereof at an angle of about 45° in a phase shifted arrangement along the lengthwise extension of projection proper 21; (b) shows projection proper 21 ... provided with two branch elements extending from each side thereof at an angle of about 45° at a median location and a distal location along the lengthwise extension thereof; (c) shows projection proper 21 ... provided with one branch element extending from each side thereof at an angle of about 45° at a median location along the lengthwise extension thereof; and (d) shows projection proper 21 ... provided with two branch elements extending from only one side thereof at an angle of about 45°. (e) shows projection proper 21 ... provided on each side thereof with semispherical branch elements 3 and with a spherical branch element 3 situated at the distal end thereof. Projections proper 21 ... may be provided with a single or a plurality of branch elements 3.

Projections proper 21 ..., 22 ... and individual branch elements 3 may be provided with cross sections that constrict going from the basal end to the distal end thereof; also, the distal ends of projections proper 21 ..., 22 ... and individual branch elements 3 may be situated at equal distances from the center of shaft member 1, with these distal ends being rounded.

Figure 7:
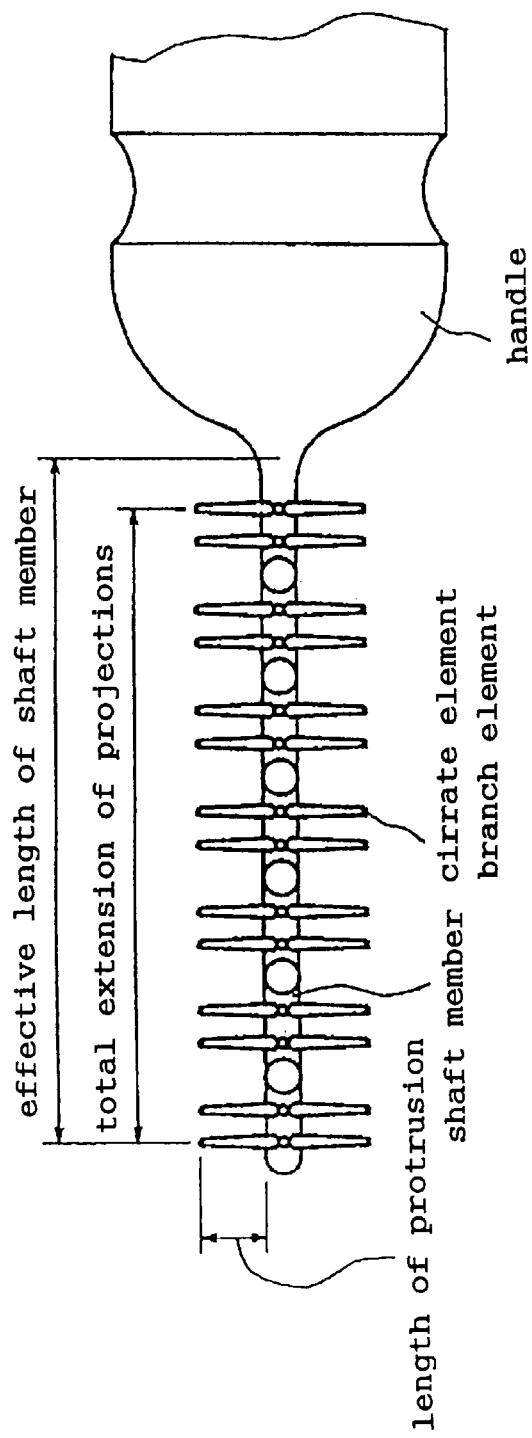
FIG. 7 is an illustrative diagram showing the size of the interdental cleaning tool.

In FIG. 1 and FIG. 3, 7 indicates the location of an ejector (ejector pin).

Figure 5:
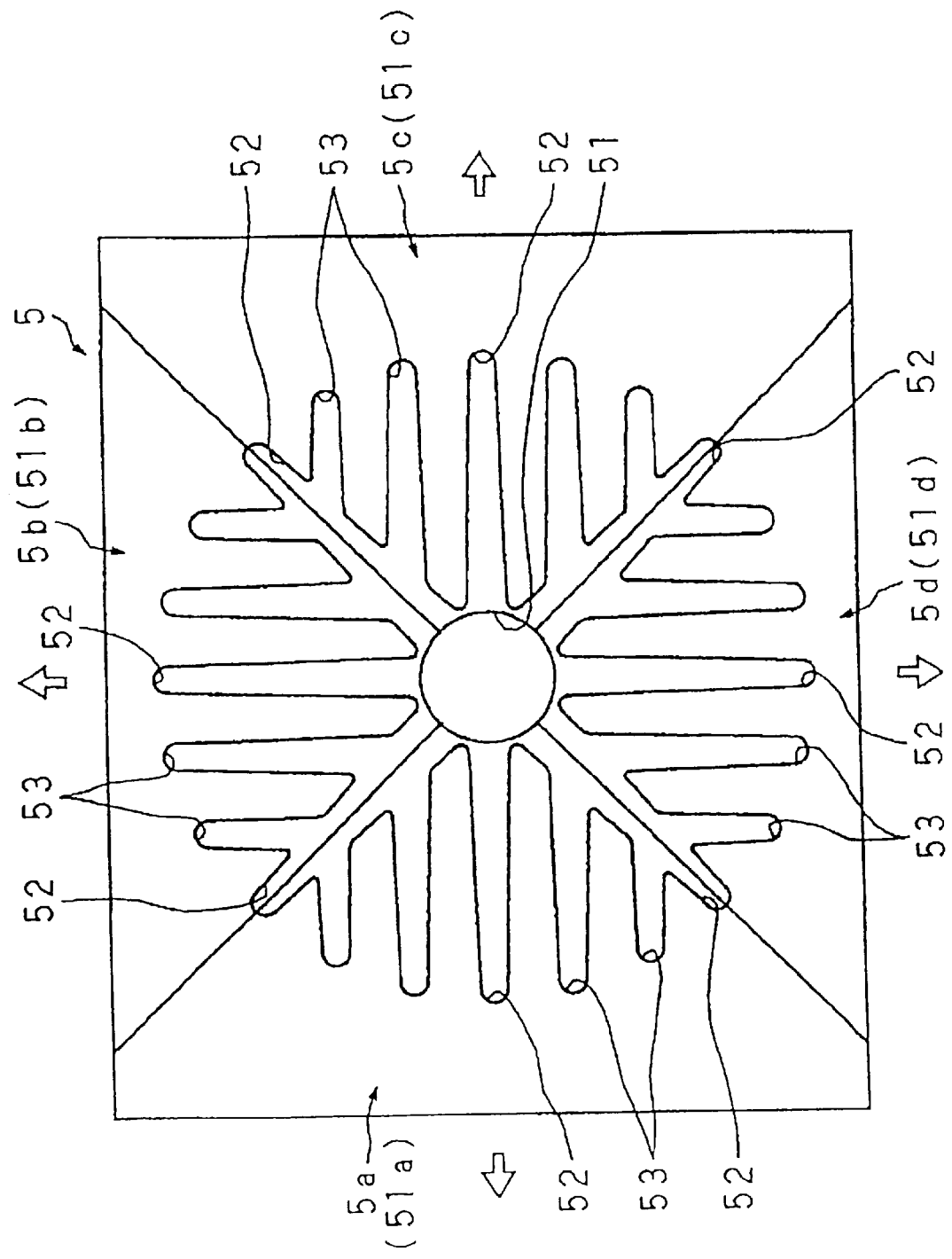
FIG. 5 is a side view of an injection mold, showing the manufacturing method for the interdental cleaning tool of the invention.

FIG. 5 is a side view of an injection mold, showing the manufacturing method for an interdental cleaning tool having the constitution described above.

The manufacturing method employs a mold comprising a first cavities 51 ... for the shaft member 1, second cavities 52 ... for projections proper 21 ..., 22 ... situated in a given plane, and third cavities 53 ... for branch elements 3 branching out from these second cavities 52 ...; an injection mold 5 comprising first molds 5a, 5b, 5c, 5d created by dividing diametrically into four sections along the axis of shaft member 1, and further comprising a third mold (not shown) comprising a fourth cavity (not shown) for molding the handle 4 and split into four sections diametrically about handle 4 is used as this mold.

First molds 5a–5d are provided by means of a machining process with first and second cavities 51 and 52 for molding one-fourth of the circumference of shaft member 1, one-fourth of adjacently situated projections proper 21, one-fourth of projections proper 22 situated therebetween, one-fourth of branch elements 3 provided to projections proper 21, and one-fourth of third cavities 53 incised therein.

Figure 6:
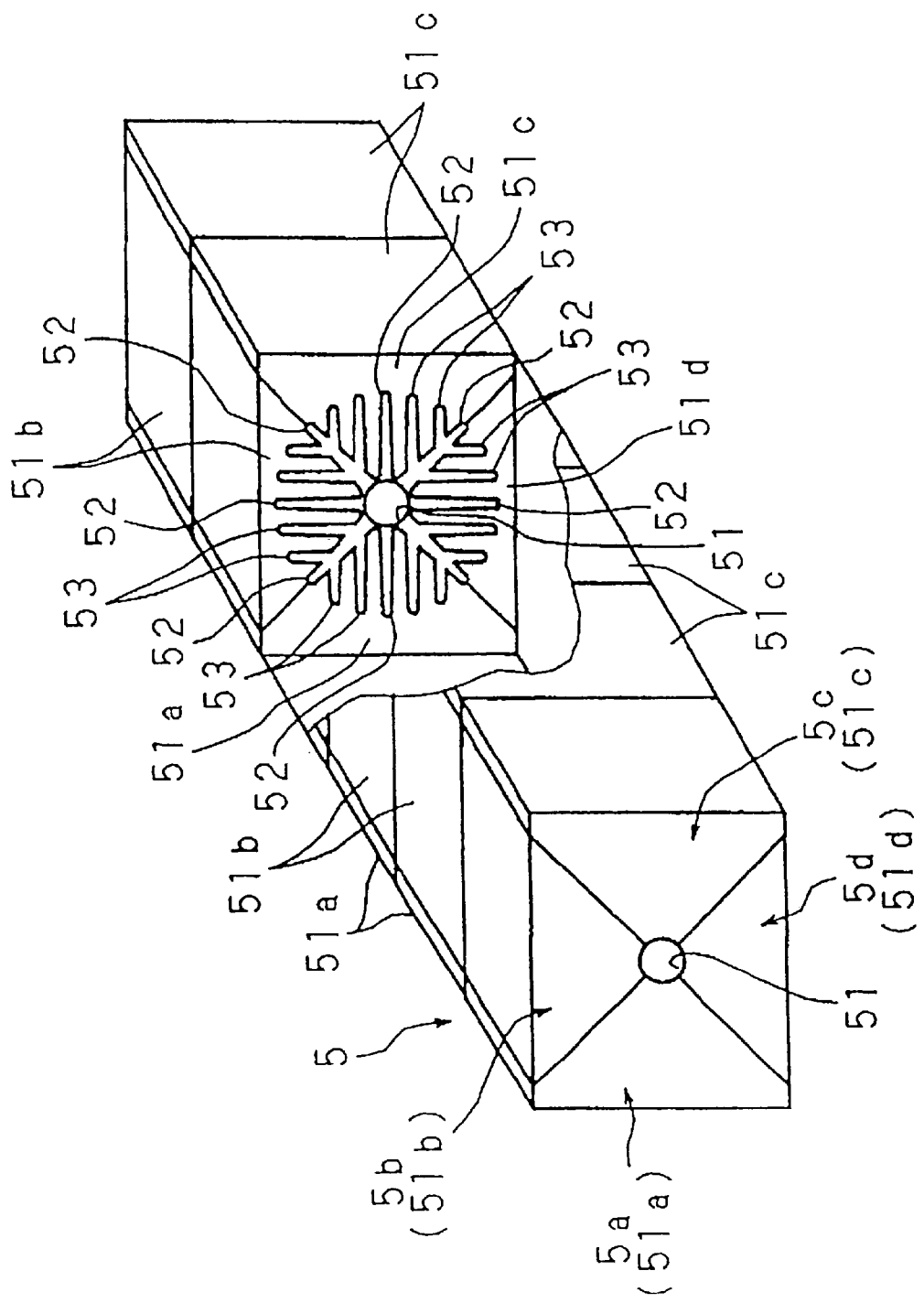
FIG. 6 is a perspective view of first molds for the interdental cleaning tool of the invention, split along the axis of the shaft member.

FIG. 6 is a perspective view of first molds 5a–5d split along the axis of the shaft member 1.

First molds 5a–5d are further divided in the axial direction of shaft member 1 into a plurality of second molds 51a ..., 51b ..., 5c ..., and 51d ... (split molds). These second molds 51a ... –51d ... are divided into thicknesses of 0.1–2 mm depending on the number of first and projections proper 21 ..., 22 ... to be produced in the axial direction of the shaft member, with the parting faces of these second molds 51a ... –51d ... each being provided with one-fourth of first and second cavities 51 ..., one-fourth of 52 ..., and one-fourth of third cavities 53 ... incised therein.

After being incised with one-fourth of first and second cavities 51 ..., one-fourth of 52 ..., and one-fourth of third cavities 53 ..., split second molds 51 ... –51d ... (split molds) are assembled at their parting faces and retained by four mold retainers (not shown), these mold retainers and second molds 51a ... –51d ... together constituting first molds 5a–5d. Molds 5a–5d are then connected with the third mold.

The mold parting faces are utilized for expelling gas present in the cavities. For example, utilizing the parting faces (mating faces) of second molds 51a ... –51d ... (split molds), any gas present in first and second cavities 51 ..., 52 ... and third cavities 53 ... can be expelled from first molds 5a–5d as molten synthetic resin enters and fills first and second cavities 51 ..., 52 ... and third cavities 53 .... The parting faces of second molds 51a ... –51d ... may be provided with gas venting recesses 5 to 15 μm deep communicating with the distal portions of first and second cavities 51 ..., 52 ... and third cavities 53 ... to aid in gas venting.

The parting faces of first molds 5a–5d and the third mold for molding the handle having the constitution described above are mated for manufacture of the interdental cleaning tool.

Manufacture may be accomplished by injecting molten synthetic resin through an inlet provided to an end of the third mold to fill a fourth cavity (not shown), first cavities 51 ... second cavities 52 ..., and third cavities 53 ... to effect integral molding of shaft member 1, projections 2 ..., branch elements 3 ..., and handle 4. During manufacture, as synthetic resin enters and fills second cavities 52 ... and third cavities 53 ..., any gas present in second cavities 52 ... and third cavities 53 ... is expelled through gaps resulting from surface roughness on the parting faces of second molds 51a ... –51d ... and through the gas venting recesses, allowing the synthetic resin to consistently enter second cavities 52 ... and third cavities 53 ... and fill them to the ends thereof, thereby ensuring uniform length of first and projections proper 21 ..., 22 ..., and branch elements 3 ... extending from the distal ends thereof to the center of shaft member 1.

As second molds 51a ... –51d ... may range in thickness from 0.1 to 2 mm, a plurality of projections proper 21 ..., 22 ... may be produced at short intervals of from 0.1 to 2 mm along the axis of shaft member 1, making it a simple matter to increase the number of projections 2 provided over the entire extension of shaft member 1. As second cavities 52 ... and third cavities 53 ... are provided at the parting faces of second molds 51a ... –51d ..., intricate incision of these second cavities 52 ... and third cavities 53 ... may be accomplished with ease. Further, a plurality of types of interdental cleaning tool having different pitch may be produced inexpensively simply by manipulating the pitch of projections 2 along the axis of the shaft member by using second molds 51 ... 51d ... of differing thickness.

Examples of synthetic resin materials which may be used are styrene, 1,2 polybutadiene, olefin, urethane, ester, amide, chlorinated polyethylene, polyvinyl chloride, or polyfluorocarbon, or other thermoplastic elastomers; polyester elastomers are chiefly used. In preferred practice HYTREL® grade 2751 ex DuPont-Toray will be used; this synthetic resin material has the following properties: a flexural modulus of 12800 kgf/cm², hardness of 75 on the durometer hardness D scale, and a melt flow index of 25 g/10 min. Where this synthetic resin material is used, shaft member 1 will not snap or bend while projections 2 and branch elements 3 will be soft; thus, snapping or bending of shaft member during insertion into gaps between teeth may be effectively prevented while yet affording a pleasant sensation during interdental cleaning.

The reasons why the use of polyester elastomers is preferred will be apparent from Table 1. Table 1 gives mechanical qualities for synthetic resin materials and service evaluations of interdental cleaning tools. The evaluations in Table 1 are for products having 0.5 mm shaft member diameter and 11 mm shaft member length. FIG. 7 is an illustrative diagram showing the size of an interdental cleaning tool produced in the preceding manner, and Table 2 gives specific dimensions thereof.

acetal resin, polycarbonate, polyester resin, cellulose plastic, or other thermoplastic resins may also be used as synthetic resin materials.

As indicated in Table 1, the thermoplastic elastomer or thermoplastic resin will in preferred practice have a flexural modulus of 6000 kgf/cm² or above and a melt flow index of 8 g/10 min or above.

The evaluations given in Table 1 are for shaft member thickness of 0.5 mm and shaft member length of 11 mm; where the shaft member is thicker or longer, improved shaft member strength and improved overall ratings may be achieved even where flexural modulus is less than 6000 kgf/cm².

Projections 2 . . . and branch elements 3 . . . of the interdental cleaning tool molded in the preceding manner have cross sections that constrict from the basal ends towards the distal ends thereof, whereby projections proper 21 . . . , 22 . . . , and branch elements 3 . . . may be imparted

TABLE 1

| synthetic resin material type | manufacturer | product name | grade | flexural modulus (kgf/cm²) | elongation (%) | hardness | melt flow index (g/10 min) | shaft member strength | shaft member durability | cirrate element sensation | cirrate element durability | overall rating |
|---|---|---|---|---|---|---|---|---|---|---|---|---|
| polyester elastomer | DuPont-Toray | HYTREL | 2751 | 12800 | 320 | durometer hardness D scale 75 | 25 | ○ | ○ | ○ | ○ | ◎ |
| | | | 7247M | 6400 | 339 | durometer hardness D scale 70 | 49 | Δ | Δ | ○ | ○ | Δ |
| | | | 5557M | 2400 | 450 | durometer hardness D scale 55 | 43 | X | Δ | ◎ | ○ | X |
| polyamide 6,6 | Asahi Chemical Industry | Leona | 1300S | 29000 | 250 | Rockwell hardness M80 | 10< | ◎ | ○ | Δ | ○ | ○ |
| aliphatic polyketone | Shell Japan | Carilon | RDP202 | 14280 | 350 | — | 50 | ◎ | ○ | Δ | ○ | ○ |
| polyacetal resin | Polyplastics | JURACON | M90-44 | 26400 | 60 | Rockwell hardness M80 | 9 | ◎ | ◎ | X | Δ | Δ |
| polyethylene resin | Asahi Chemical Industry | Suntec HD | J240 | 19000 | 500 | Shore hardness D scale 74 | 5 | ○ | X | X | X | X |

◎: excellent,
○: good,
Δ: poor,
X: very poor

TABLE 2

| | shaft member thickness (mm) | cirrate element projection thickness (mm) | projection length (mm) | projection total length (mm) | shaft member effective length (mm) | cirrate element projection/branch element density (number per mm) |
|---|---|---|---|---|---|---|
| A | 0.3–2.0 | 0.03–0.30 | 0.5–3 | 3–14 | 3–16 | 8–80 |
| B | 0.4–1.5 | 0.04–0.25 | 0.5–3 | 4–12 | 4–14 | 8–64 |
| C | 0.5–1.2 | 0.05–0.20 | 0.5–3 | 5–10 | 5–12 | 8–48 |

In Table 2, example B is preferred to A, and C is preferred to B.

The desirability indicated here represents postulated suitability giving overall consideration factors such as ease of insertion, organoleptic qualities, size of the interdental gap to be cleaned, suitability to molding processes, etc.

Vinyl chloride resin, vinyl acetate resin, aromatic polyketone resin, polystyrene, ABS resin, acrylic resin, polyethylene, polypropylene, fluororesin, polyamide resin, with a suitable degree of strength and the tips thereof with high cleaning performance of minute features during interdental cleaning by means of inserting shaft member 1 into a gap between teeth. As the distal ends of projections proper 21 . . . , 22 . . . , and branch elements 3 . . . are rounded, projections 2 . . . and branch elements 3 . . . produce a soft sensation against the teeth and gums as shaft member 1 is inserted into a gap between teeth.

Figure 10:
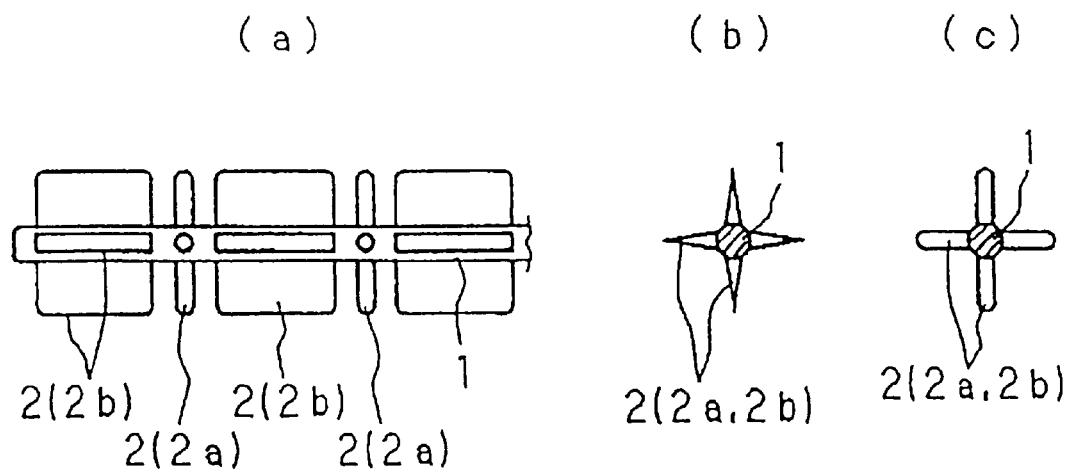
FIG. 10 depicts another embodiment of projections of the interdental cleaning tool of the invention, (a) being a front view and (b) and (c) being transverse sectional side views.
Figure 11:
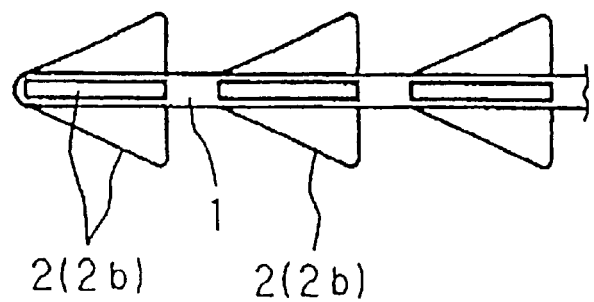
FIG. 11 is a front view depicting another embodiment of projections of the interdental cleaning tool of the invention.
Figure 12:
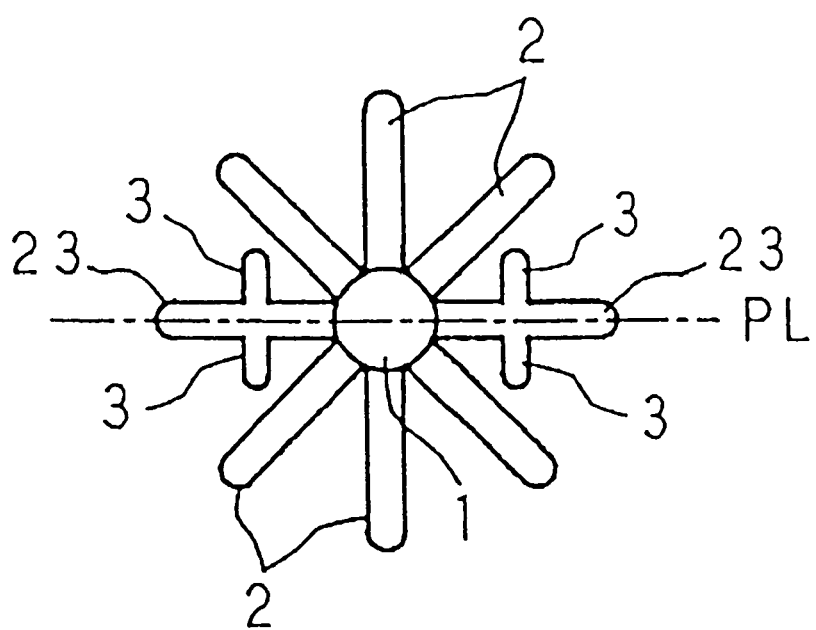
FIG. 12 is a side view depicting another embodiment of projections of the interdental cleaning tool of the invention.

FIGS. 8 to 12 depict other embodiments for projections. FIG. 8(a), FIG. 9(a), FIG. 10(a), and FIG. 11 are front views; FIG. 8(b), FIGS. 9(b)–(d), FIGS. 10(b),(c), and FIG. 12 are side views.

Figure 8:
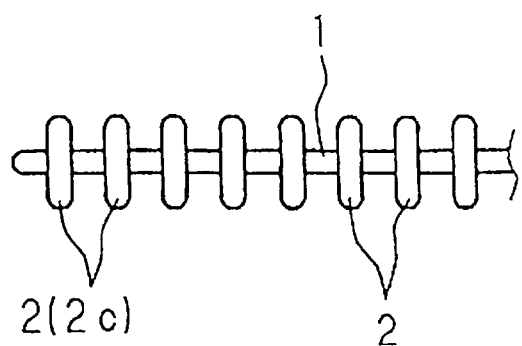
FIG. 8 depicts another embodiment of projections of the interdental cleaning tool of the invention, (a) being a front view and (b) being a transverse sectional side view.
Figure 8:
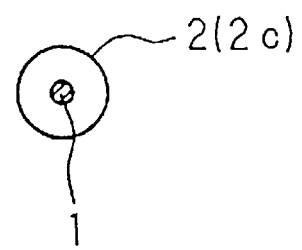
Figure 9:
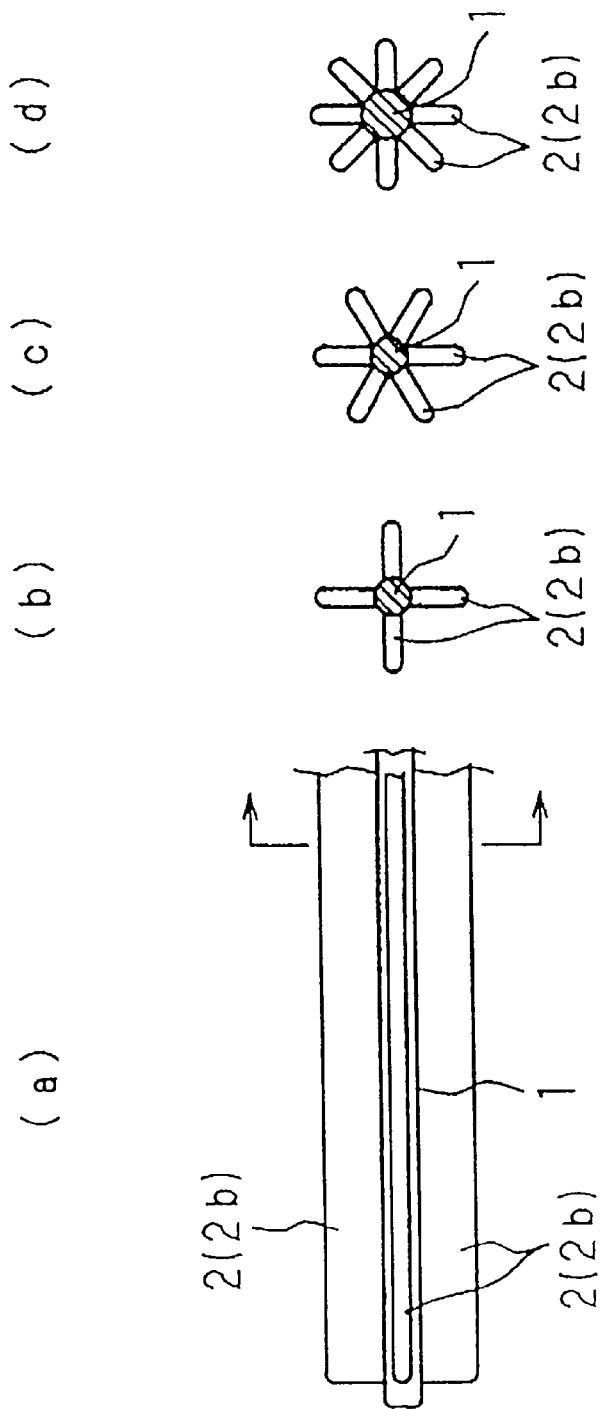
FIG. 9 depicts another embodiment of projections of the interdental cleaning tool of the invention, (a) being a front view and (b) to (d) being transverse sectional side views.

FIG. 8 depicts projections 2 . . . composed of disk elements 2c, a plurality thereof being arranged at desired intervals along the axis of shaft member 1; FIG. 9 depicts projections 2 . . . composed of pinnulate elements 2b elongated in the axial direction, a plurality thereof being arranged at desired intervals about the circumference of shaft member 1 in the manner depicted in FIGS. 9(b)–(d); FIG. 10 depicts projections 2 . . . comprising both cirrate elements 2a and pinnulate elements 2b arranged in alternating fashion in the axial direction of shaft member 1; FIG. 11 depicts the use of a plurality of pinnulate elements 2b as projections 2 . . . , a plurality thereof being arranged at desired intervals codirectional with the axis and circumference of shaft member 1; and FIG. 12 depicts cirrate elements 23 extending along the axis of shaft member 1 at a location corresponding to the parting portion PL of a two-section split mold, and having integrally formed therewith branch elements 3 that extend in a direction intersecting in substantially perpendicular fashion the lengthwise axis of the cirrate element 23. Other features and operation are analogous to those of the products depicted in FIGS. 1 to 4, equivalent elements being assigned the same symbols, dispensing with detailed description and operation thereof.

Where projections 2 . . . are pinnulate elements 2b, the thickness thereof will be 0.2 mm or smaller and in preferred practice 0.15 mm or smaller. The height (height in the diametral direction of the shaft member) of pinnulate elements 2b is 0.5 mm or greater over the entire length thereof. Pinnulate element 2b may be rounded at the apical portion thereof to produce a semicircular section and have the same given thickness from the apical portion to the basal end thereof, as depicted in FIG. 10(c), or may constrict towards the apical portion thereof, as shown in FIG. 10(b). In FIGS. 9 to 11, a single or a plurality of pinnulate elements 2b may be provided. Where the number of pinnulate elements 2b is small (one or two), pinnulate elements 2b may be arranged in a spiral configuration.

Where projections 2 . . . comprise both cirrate elements 2a and pinnulate elements 2b, these may be arranged in alternating fashion in the direction of the axis of shaft member 1, as shown in FIG. 10, and may be arranged randomly along the axis and circumference of shaft member 1. Projections 2 . . . provided to shaft member 1 may be composed of combinations of the projections depicted in FIGS. 8 to 12.

In FIG. 8, projections 2 . . . are disc-shaped elements 2c, affording better cleaning performance with a small number of projections 2 . . .

In FIGS. 9 to 11, the provision of pinnulate elements enhances cleaning performance by individual projections and contributes to projection durability.

In FIG. 12, both projections proper 23 and branch elements contribute to interdental cleaning, affording further enhanced cleaning performance.

According the embodiments described above, shaft member 1, projections 2 . . . , branch elements 3, and handle 4 have an integrally molded configuration; however, in an alternative configuration handle 4 may be molded separately, and the end of shaft member 1 attached to the handle.

According to the manufacturing method described previously, there are provided third cavities 53 . . . that branch off from second cavities 52 . . . to allow for integral molding of projections 2 . . . and branch elements 3; in an alternative configuration, however, third cavities 53 . . . may be dispensed with, providing first and second cavities 51 . . . , 52 . . . to allow for integral molding of projections proper 21 . . . , 22 . . .

FIGS. 13(a), (b), and (c) are longitudinal sectional front views depicting other embodiments of the shaft member portion of the interdental cleaning tool of the invention.

FIG. 13(a) shows insert molding wherein the shaft member 1 has a core element 6 inserted therein which consists of a material having a higher flexural modulus than does the synthetic resin for the molding shaft member 1 and projections 2 . . . , for example, a highly elastic synthetic resin, or of highly rigid metal wire, such as piano wire. FIG. 13(b) shows two-color molding wherein projections 2 . . . and the skin portion 1a sheathing core element 6 are molded from synthetic resin; handle 4 is integrally molded with a core element 6 consisting of synthetic resin having a higher flexural modulus than the flexural modulus of the synthetic resin from which are molded projections 2 . . . and skin portion 1a; and core element 6 consists of different resin than the other members. In FIG. 13(c), the core element of FIG. 13(b) is provided with at least one, and in preferred practice a plurality of, retainer projections 61, with the constitution and operation thereof being otherwise identical to those depicted in FIG. 1 to FIG. 4, equivalent elements being assigned the same symbols and dispensing with detailed description and operation thereof.

Figure 13:
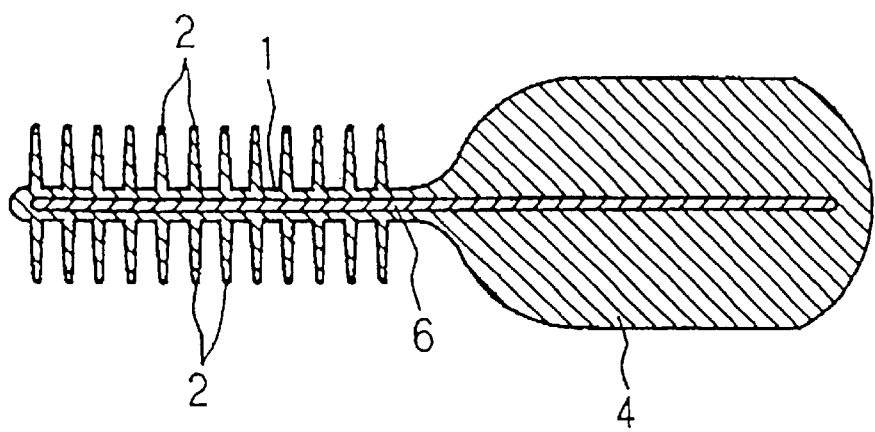
FIG. 13 shows longitudinal sectional front views depicting other embodiments of the shaft member portion of the interdental cleaning tool of the invention.
Figure 13:
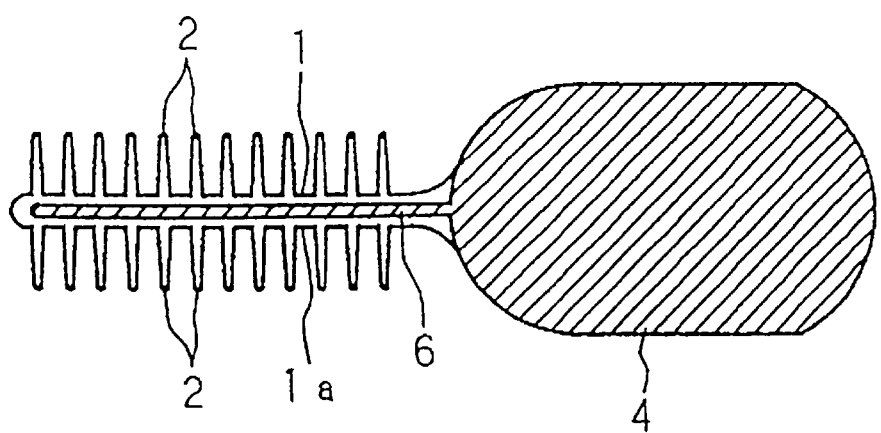
Figure 13:
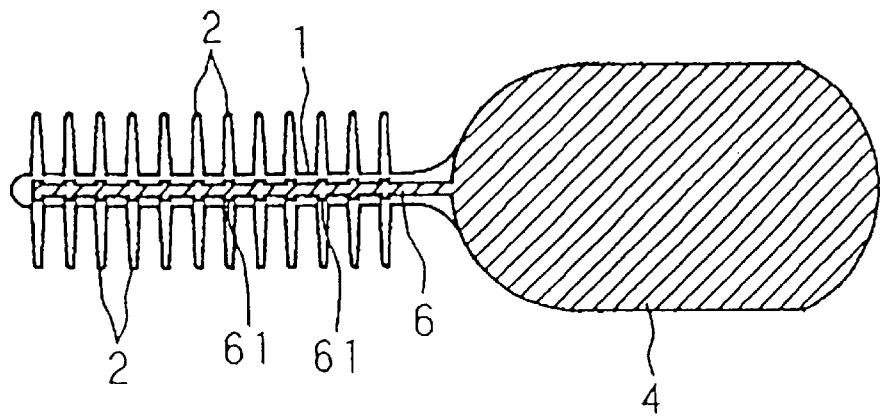

In FIG. 13, by endowing projections 2 . . . that participate in interdental cleaning with flexural modulus lower than the flexural modulus of shaft member 1, projections 2 . . . may be endowed with good flexibility; further, by endowing shaft member 1 with flexural modulus higher than the flexural modulus of projections 2 . . . excessive flexure of shaft member 1 may be prevented and shaft member strength enhanced. Where core element 6 consists of metal, a low-elongation material may be used to effectively prevent bending of the shaft member.

FIGS. 14(a), (b), and (c) show representative diagrams of molds for molding synthetic resins differing in flexural modulus.

FIG. 14(a) depicts an injection mold 5 comprising a fourth cavity 54 for the handle and further comprising first and second filling openings 55a, 55b which open into this cavity 54. Through these first and second filling openings 55a, 55b are injected, simultaneously or with a predetermined time lag, synthetic resins with differing flexural modulus; FIG. 14(b) depicts an injection mold 5 comprising a first filling opening 55a that opens into a fourth cavity 54 for the handle, and a third filling opening 55c that opens into first cavity 51 for shaft member 1, synthetic resins with differing flexural modulus being introduced through first and third filling openings 55a, 55c. FIG. 14(c) depicts an injection mold 5 comprising a first filling opening 55a that opens into a fourth cavity 54 for the handle, a plurality of communicating paths 56 that communicate with the distal ends of second cavities 52, and a fourth filling opening 55d that communicates with these communicating paths 56, synthetic resins with differing flexural modulus being injected through first and fourth filling openings 55a, 55d, with the constitution and operation thereof being otherwise identical to those depicted in FIG. 1 to FIG. 4, equivalent elements being assigned the same symbols and dispensing with detailed description and operation thereof.

Figure 14:
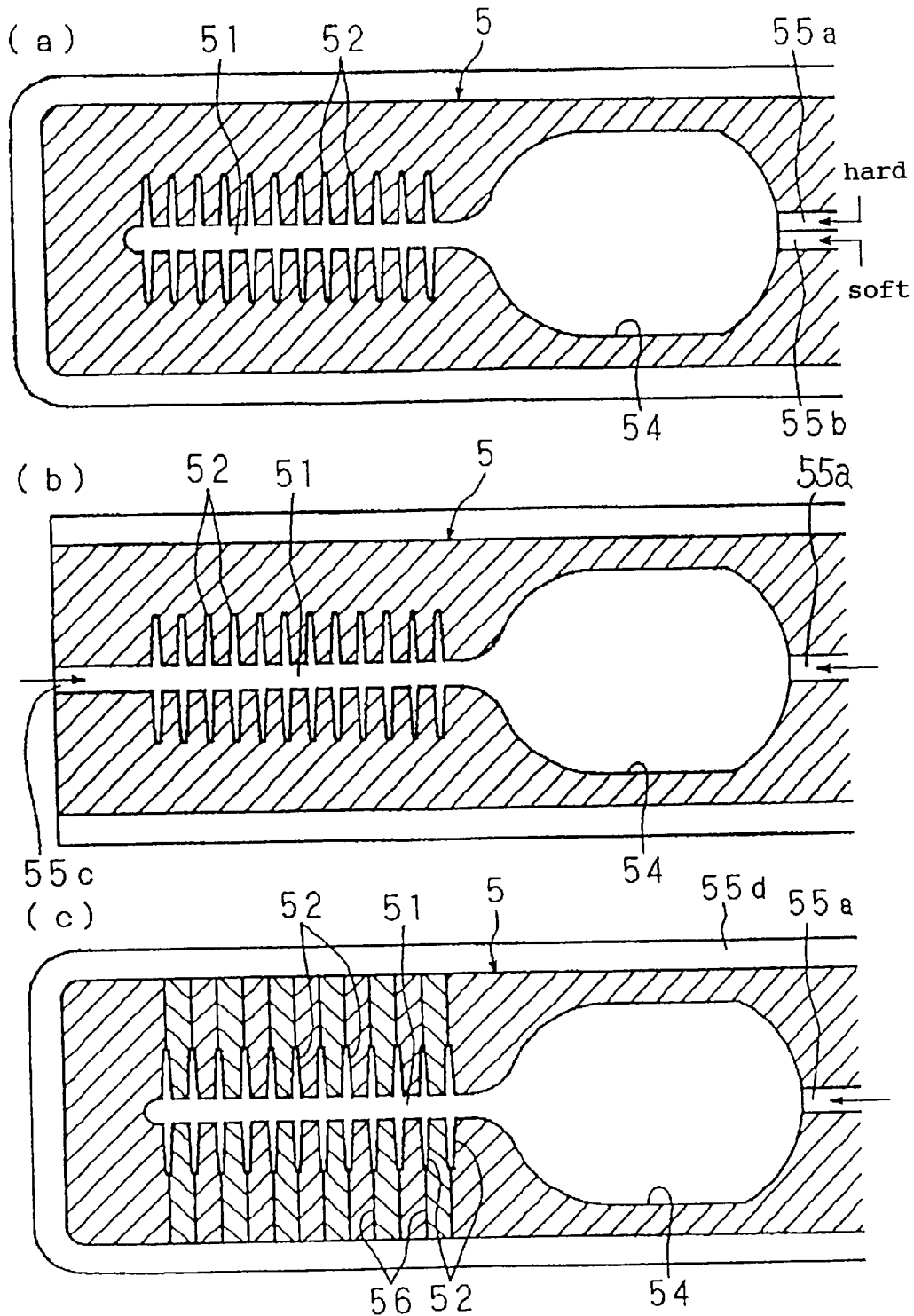
FIG. 14 shows representative diagrams of molding of the interdental cleaning tool of the invention using synthetic resins differing in flexural modulus.

In FIG. 14, by means of injecting through first filling opening 55a synthetic resin having a higher flexural modulus than the flexural modulus of projections 2 . . . , it is possible to produce projections 2 . . . for interdental cleaning that have flexural modulus lower than the flexural modulus of shaft member 1, whereby it is possible to endow projections 2 . . . with good flexibility while imparting to shaft member 1 a flexural modulus higher than the flexural modulus of projections 2 . . . so as to prevent excessive flexure of shaft member 1 and enhance the strength of the shaft member.

FIG. 15 to FIG. 21 are representative diagrams of molds employable in the method for manufacturing the interdental cleaning tool of the invention.

Figure 15:
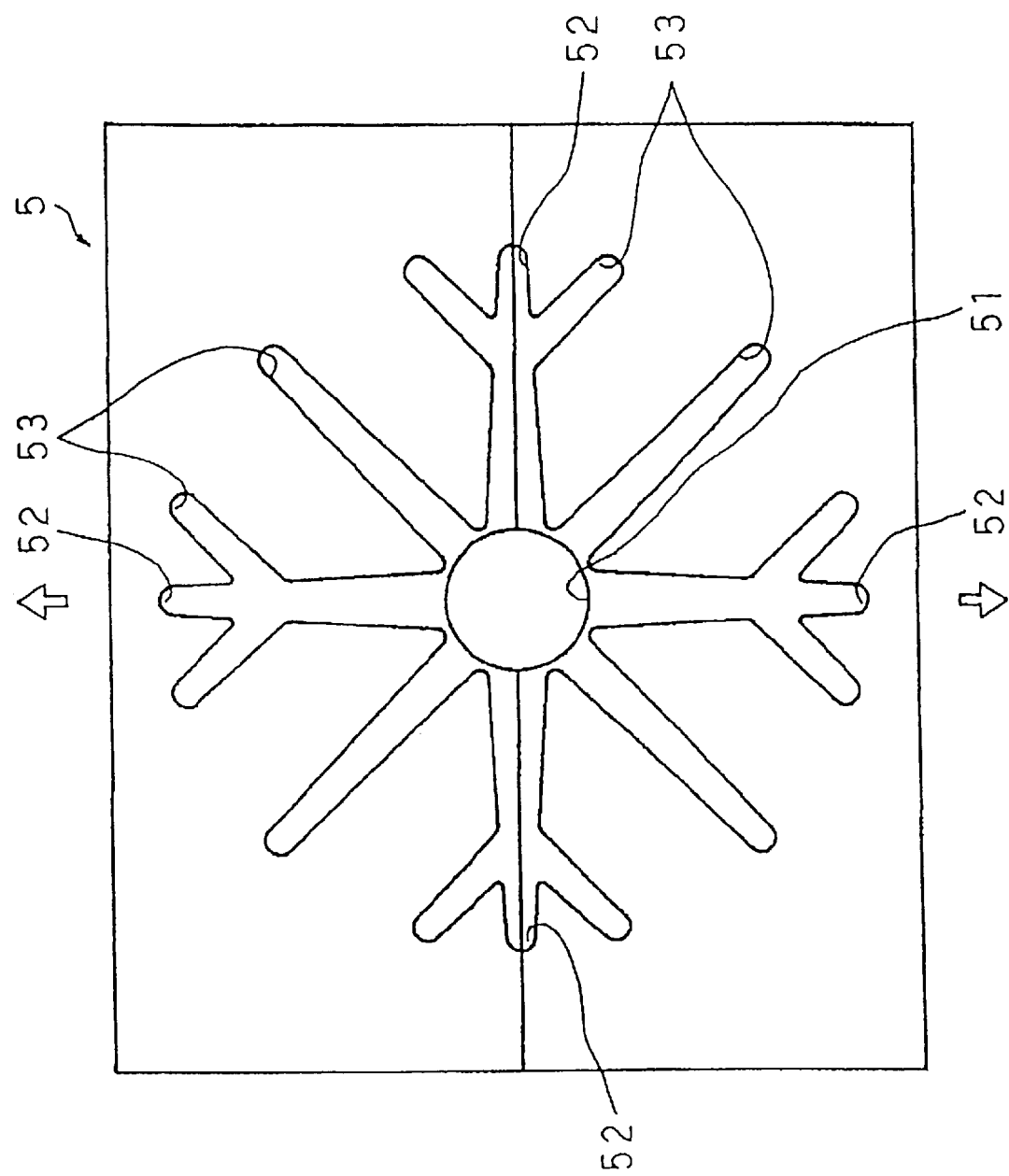
FIG. 15 is a representative diagram of a mold employable in the method for manufacturing the interdental cleaning tool of the invention.

FIG. 15 depicts a mold split into front and back halves in the circumferential direction of the shaft member. That is, FIG. 15 comprises a plurality of second cavities 52 extending in the direction of movement of the aforementioned first molds 5a . . . 5d . . . (which, it will be recalled, are assembled in such a way as to be moveable in the radial direction of shaft member 1), and third cavities 53 arranged in directions intersecting therewith. With this mold, third cavities 53 intersect the radial direction (direction of movement) at angles such that, when first molds 5a . . . 5d . . . move in the radial direction, molded portions present within third cavities 53 undergo elastic deformation sufficient to allow first molds 5a . . . 5d . . . to be moved in the radial direction. The constitution and operation are otherwise identical to those depicted in FIG. 5 and FIG. 6, equivalent elements being assigned the same symbols and dispensing with detailed description and operation thereof.

According to this manufacturing method, third cavities 53 . . . are formed so as to prevent restriction of first molds 5a . . . 5d . . . in the directions of movement thereof, whereby branch elements 3 . . . may be molded using a smaller number of first molds 5a . . . 5d . . . , affording further reductions in production costs so that an interdental cleaning tool comprising projections 2 . . . and branch elements 3 . . . may be produced at lower cost.

Figure 16:
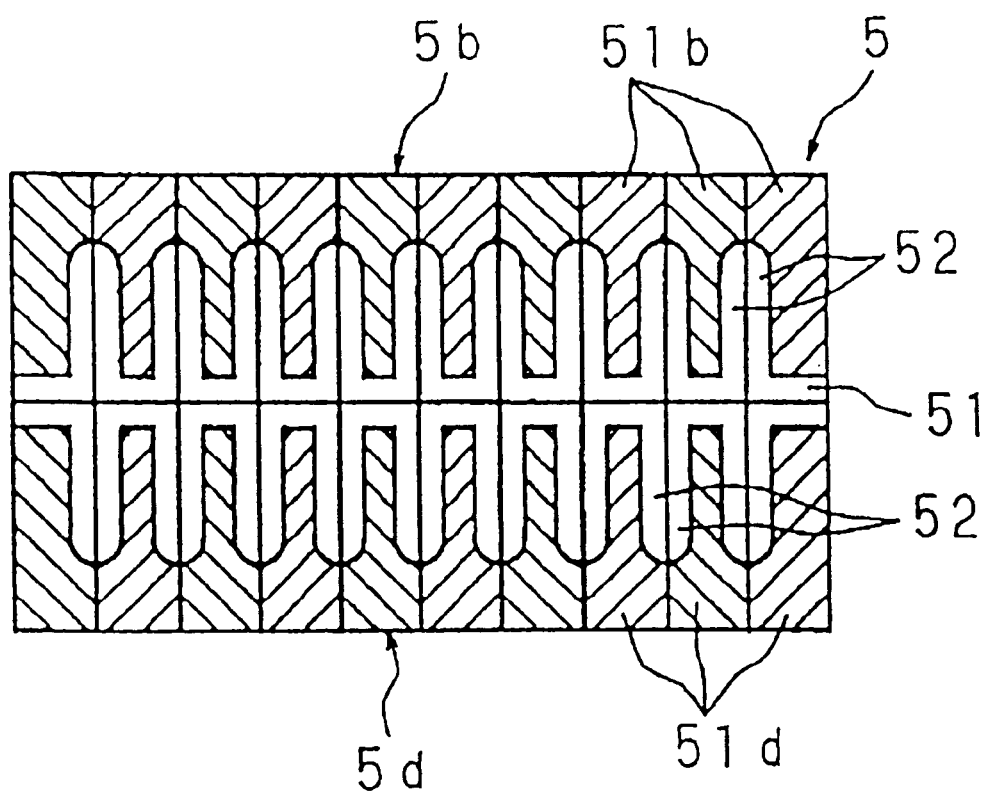
FIG. 16 is a representative diagram of a mold employable in the method for manufacturing the interdental cleaning tool of the invention.
Figure 17:
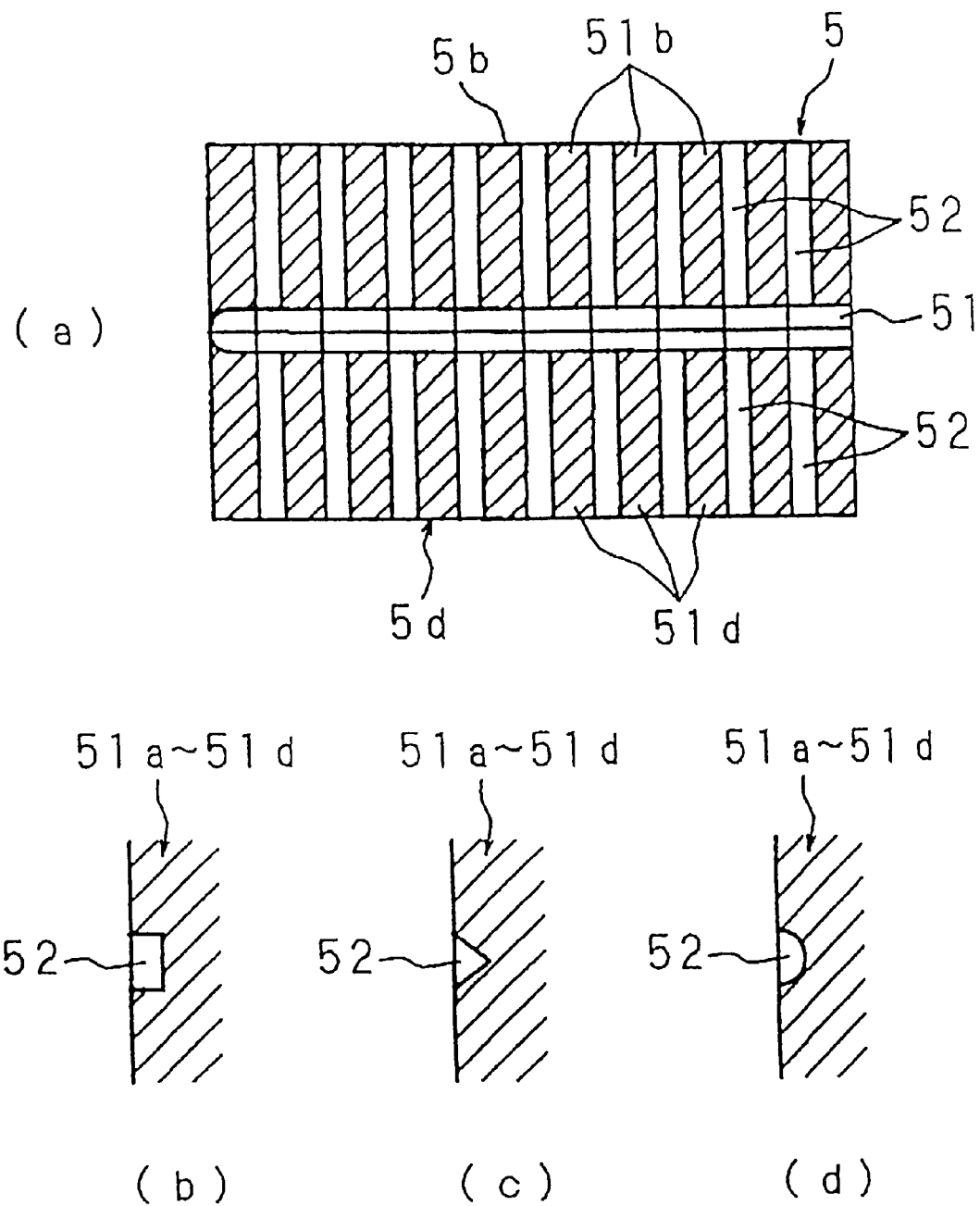
FIG. 17 shows a representative diagram of a mold employable in the method for manufacturing the interdental cleaning tool of the invention.

FIG. 16 is an injection mold 5 comprising first molds 5a . . . 5d . . . and second molds 51a . . . 51d . . . , the parting faces of second molds 51a . . . 51d . . . being provided on a first side face and a second side face thereof with second cavities 52 . . .

FIG. 17(a) is an injection mold comprising the aforementioned first molds 5a . . . 5d . . . and second molds 51a . . . 51d . . . , the parting faces of second molds 51a . . . 51d . . . being provided on a first side face only with second cavities 52 . . . Possible sectional configurations for second cavities 52 . . . are the square configuration shown in FIG. 17(b), the triangular configuration shown in FIG. 17(c), and the semicircular configuration shown in FIG. 17(d).

Figure 18:
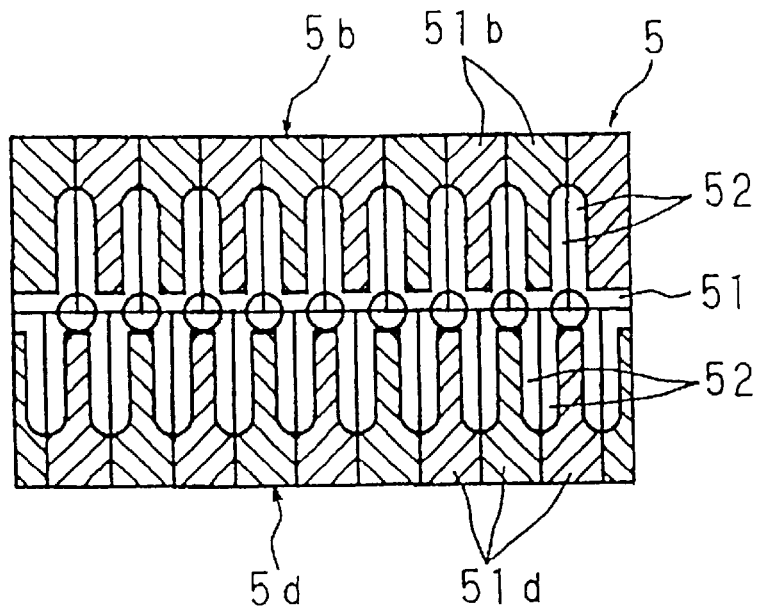
FIG. 18 is a representative diagram of a mold employable in the method for manufacturing the interdental cleaning tool of the invention.

FIG. 18 is an injection mold comprising the aforementioned first molds 5a . . . 5d . . . and second molds 51a . . . 51d . . . , the parting faces of second molds 51a . . . 51d . . . being provided on a first side face and a second side face thereof with second cavities 52 . . . , with the aforementioned first molds 5a . . . 5d . . . being assembled in such a way that parting faces of second molds 51a . . . 5d . . . are offset in zigzag fashion in the axial direction shaft member 1, whereby it is possible to mold projections 2 . . . arranged offset in zigzag fashion in the axial direction shaft member 1.

Figure 19:
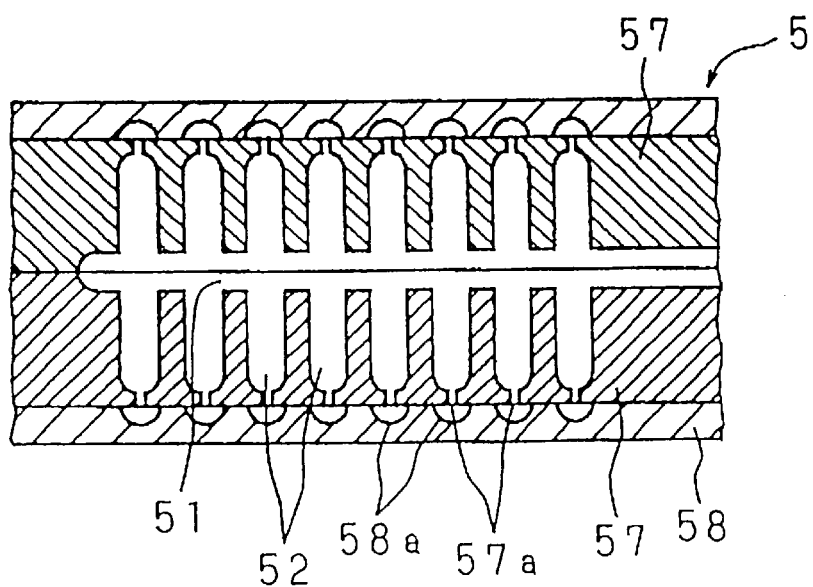
FIG. 19 is a representative diagram of a mold employable in the method for manufacturing the interdental cleaning tool of the invention.

FIG. 19 comprises fourth molds 57 . . . divided into a plurality of segments in the axial direction of shaft member 1, and a gas vent mold 58 arranged about fourth molds 57 . . . , the parting sections of fourth molds 57 . . . being provided with first and second cavities 51 . . . , 52 . . . , the fourth molds 57 . . . and gas vent mold 58 being provided with a plurality of communicating paths 57a, 57b communicating with the distal end portions of second cavities 51 . . . , 52 . . . , and mold 57 being provided with an injection port (not shown) that communicates with first cavity 51.

In FIG. 19, communicating paths 58a are placed in communication with a negative pressure source (e.g., a vacuum pump, etc.), communicating paths 57a, 58a are brought to negative pressure, and synthetic resin in injected into first cavity 51 from the injection port, whereby the synthetic resin can flow to the tips of the second cavities, producing projections 2 . . . of desired length, with the length of projections 2 . . . being uniform.

Figure 20:
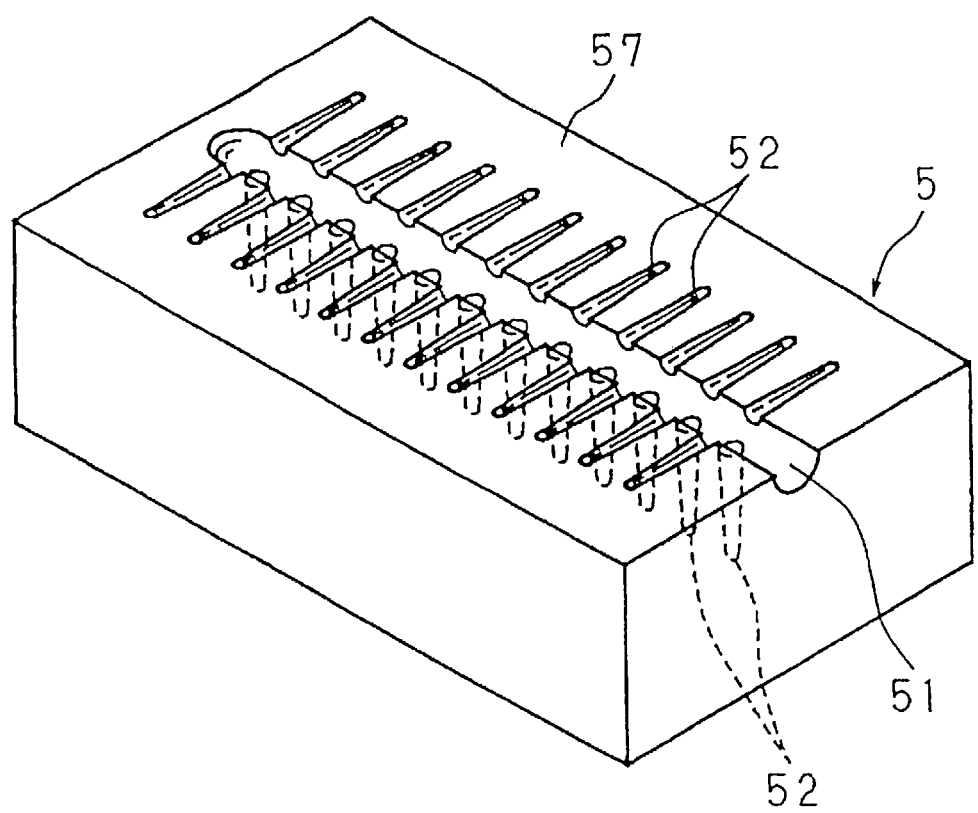
FIG. 20 is a representative diagram of a mold employable in the method for manufacturing the interdental cleaning tool of the invention.

FIG. 20 is provided with first and second cavities 51 . . . , 52 . . . situated on the parting faces of fourth molds 57 . . . which are divided into a plurality of sections (two, for example) along the axis of shaft member 1, and with second cavities 52 . . . which extend in directions intersecting parting faces, and preferably intersecting therewith at right angles.

In FIG. 20, as it is possible to produce an interdental cleaning tool provided with a plurality of projections 2 . . . arranged in the axial direction of shaft member 1 using a mold divided into two sections along the axis of shaft member 1, production can be accomplished in fewer steps than methods employing wire, affording lower costs in interdental cleaning tool production.

Figure 21:
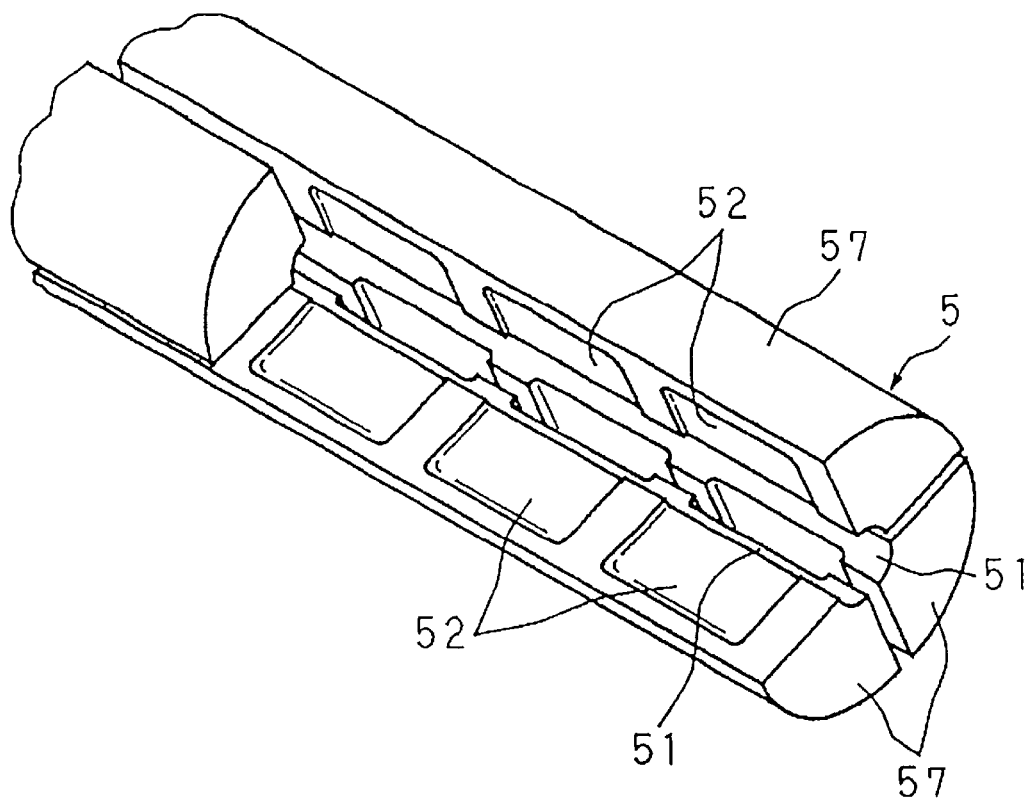
FIG. 21 is a representative diagram of a mold employable in the method for manufacturing the interdental cleaning tool of the invention.

FIG. 21 is provided with first and second cavities 51 . . . , 52 . . . situated on the parting faces of fourth molds 57 . . . which are divided into a plurality of sections (four, for example) along the axis of shaft member 1, the constitution and operation of FIG. 15 to FIG. 20 being otherwise identical to those depicted and FIG. 1 to FIG. 4, with equivalent elements being assigned the same symbols and dispensing with detailed description and operation thereof.

In FIG. 21, as it is possible to produce an interdental cleaning tool provided with a plurality of projections 2 . . . arranged in the axial direction of shaft member 1 using a mold divided into four sections along the axis of shaft member 1, production can be accomplished in fewer steps than methods employing wire, affording lower costs in interdental cleaning tool production.

In the preceding embodiments, injection molds divided into three or more sections along the axis of shaft member 1 may be divided in the injection direction in the manner depicted in FIG. 21, or may be divided parallel to the aforementioned axis, the parting configuration not being limited to any particular configuration.

According to the interdental cleaning tool of the first invention, projections and a shaft member and for insertion into gaps between adjacent teeth are integrally molded from synthetic resin, affording a soft sensation against the tissues of the oral cavity during use. Further, as synthetic resin projections are integrally molded with the shaft member, variation in projection extraction force may be eliminated. Moreover, as the projections and shaft member constitute an integrally molded structure, manufacture involves a fewer number of manufacturing steps than does a corresponding product using wire, thus affording reduced cost.

Where the projection is a pinnulate member, cleaning performance by an individual projection may be enhanced and the projection may be rendered highly durable.

According to the interdental cleaning tool of the second invention, a structure is possible wherein a plurality of projections are arranged codirectional with the circumference and axis of the shaft member, affording enhanced cleaning performance. The use of a split mold facilitates intricate machining of mold cavities.

According to the interdental cleaning tool of the third invention, maximum thickness for a pinnulate member or diameter for a cirrate member participating in interdental cleaning is 0.2 mm or smaller, whereby pinnulate members or cirrate members are rendered flexible so as to give a pleasant sensation during use.

According to the interdental cleaning tool of the fourth invention, projections are 0.5 mm or greater in length with respect to the peripheral face of the shaft member, affording adequately enhanced cleaning performance.

According to the interdental cleaning tool of the fifth invention, pinnulate member density centered about the shaft member is at least 3 per 360° and cirrate member density in the axial direction of the shaft member is at least 8 per 1 mm, thereby affording sufficiently good cleaning performance.

According to the interdental cleaning tool of the sixth invention, projections proper (which are unified with the shaft member) and branch members that branch therefrom in directions intersecting therewith participate in interdental cleaning, increasing the number of points of contact with the tooth, thus affording further enhanced cleaning performance.

According to the interdental cleaning tool of the seventh invention, the shaft member is provided by means of insert molding or two-color molding with a core element consisting of a material having a high flexural modulus, whereby projections which participate in interdental cleaning are endowed with good flexibility, excessive flexion of the shaft member is prevented, and shaft member strength is increased.

According to the interdental cleaning tool of the eighth invention, projections which participate in interdental cleaning are endowed with good flexibility, excessive flexion of the shaft member is prevented, and shaft member strength is increased.

According to the interdental cleaning tool of the ninth invention, there is no twisting process, as with interdental cleaning tools using wire, so that the core element may be composed of a highly rigid material such as piano wire, precluding bending of the shaft member. The use of highly rigid metal also allows the inserted core element to have smaller diameter, and the use of a shape memory alloy allows an interdental cleaning tool having become bent through to be restored by immersion in hot water.

According to the interdental cleaning tool of the tenth invention, the shaft member is integrally molded with the projections from a synthetic resin having a flexural modulus higher than the flexural modulus of the synthetic resin used for the projections, whereby the shaft member and projections can be integrally molded using within the mold one synthetic resin for the projections and another synthetic resin for the shaft member, thereby affording pliable projections, as well as increased strength of the shaft member, affording a pleasant sensation during cleaning between the teeth.

According to the interdental cleaning tool of the eleventh invention, a finished interdental cleaning tool can be molded easily by melting thermoplastic resin at a suitable temperature and flowing the melt into a mold. The product will have softer contact against oral cavity tissues than will an interdental cleaning tool having synthetic resin cirrate elements embedded in wire, as in the conventional art example.

According to the interdental cleaning tool of the twelfth invention, the exceptional recovery of the thermoplastic elastomer prevents permanent bending of the shaft member. The exceptional elasticity affords softer contact against oral cavity tissues.

According to the interdental cleaning tool of the thirteenth invention, the shaft member and projections resist bending owing to a flexural modulus of 6000 kgf/cm$^2$ or above and are rendered more highly durable; a melt flow index of 8 g/10 min or above gives the synthetic resin good flow when filling the mold, eliminating short shot in the cavities and giving a good molded shape.

According to the manufacturing method of the fourteenth invention, an interdental cleaning tool whose shaft member is provided with a plurality of projections may be molded using a mold of simple construction.

According to the manufacturing method of the fifteenth invention, the number and density of projections of an interdental cleaning tool whose shaft member is provided with a plurality of projections may be increased.

According to the manufacturing method of the sixteenth invention, as a mold section is filled with synthetic resin, gas present in the mold section can escape to the outside through gaps in the parting section (mating portions for opening the mold and mating portions of the split mold not used for opening the mold), allowing the synthetic resin to migrate up to the end of the mold section without the need to provide special gas vent openings, to give projections of desired length.

According to the manufacturing method of the seventeenth invention, intricate machining of a plurality of cavities on parting faces of a split mold may be accomplished readily, whereby it is a simple matter to produce a split mold for providing a plurality of projections along the circumference of the shaft member so that manufacturing costs for the interdental cleaning tool may be reduced. Further, gas present in a cavity can be vented through a gap between the parting faces, allowing the synthetic resin to migrate up to the end of the cavity without the need to provide a special gas vent opening.

According to the manufacturing method of the eighteenth invention, spacing between projections in the direction of the axis of the shaft member is small, viz., 0.1 to 2 mm, so that it is a simple matter to increase the number and density of projections arranged over the entire lengthwise extension of the shaft member.

According to the manufacturing method of the nineteenth invention, it is a simple matter to form cavities for a plurality of projections on the parting faces of mold split into three or more sections, whereby an interdental cleaning tool having a plurality of projections arranged codirectional with the axis and circumference of the shaft member can be manufactured at reduced cost.

What is claimed is:

1. An interdental cleaning tool comprising a plurality of projections on the peripheral face of a shaft member, wherein the projections are cirrate members, said cirrate members comprising a cirrate projection proper extruded on the outer peripheral surface of said shaft member and at least one branch member branched and extruded from the projection proper, and extending in a direction that intersects the axis of the projection proper;

wherein a density of said cirrate members is on average at least 8 per 1 mm of a width in the axial direction along the outer peripheral surface of the shaft member, the shaft member and cirrate members being integrally molded from synthetic resin.

2. The interdental cleaning tool according to claim 1, wherein said at least one branch member is cirrate, and both of said projection proper and each cirrate branch member branched and extruded from said projection proper are in a same projection plane.

3. The interdental cleaning tool according to claim 2,
wherein the projection plane is perpendicular to the axis of the shaft member.

4. The interdental cleaning tool according to claim 2,
wherein four cirrate members comprising said projection proper and said at least one branch member branched from said projection proper are provided with equal gaps in said projection plane, and said at least one branch member of each cirrate member are extending to said projection proper at substantially 45°.

5. The interdental cleaning tool according to any one of claims 1 to 4,
wherein said cirrate members are molded using a mold provided with cavities for forming said cirrate members, situated on parting faces thereof that intersect the axis of the shaft member or on parting faces containing an axial line of the shaft member which is parted along the shaft member.

6. The interdental cleaning tool according to any one of claims 1 to 4,
wherein said cirrate members' diameter is 0.2 mm or smaller.

7. The interdental cleaning tool according to any one of claims 1 to 4,
wherein said cirrate members are 0.5 mm or longer in length.

8. The interdental cleaning tool according to any one of claims 1 to 4,
wherein said shaft member is molded from a synthetic resin having a flexural modulus higher than the flexural modulus of the synthetic resin used for the cirrate members.

9. The interdental cleaning tool according to any one of claims 1 to 4,
wherein said shaft member and cirrate members are injection molded from thermoplastic resin.

10. The interdental cleaning tool according to any one of claims 1 to 4,
wherein said shaft member and cirrate members are injection molded from a thermoplastic elastomer.

11. The interdental cleaning tool according to any one of claims 1 to 4,
wherein said shaft member and cirrate members are injection molded from a thermoplastic resin or thermoplastic elastomer having flexural modulus of 6000 kgf/cm2 or above and a melt flow index of 8 g/10 min or above.

12. The interdental cleaning tool according to claim 1,
wherein said shaft member includes a core element consisting of a material having a flexural modulus higher than the flexural modulus of the synthetic resin, produced by insert molding or two-color molding.

13. The interdental cleaning tool according to claim 12,
wherein the material for the core element of said shaft member is synthetic resin having a flexural modulus higher than the flexural modulus of the synthetic resin used for said cirrate members.

14. The interdental cleaning tool according claim 12,
wherein the material for the core element of said shaft member is metal.

15. An interdental cleaning tool manufacturing process for manufacturing an interdental cleaning tool according to claim 1, the process comprising steps of:
providing an injection mold comprising a cavity for molding the shaft member and the cirrate members of the interdental cleaning tool;
wherein the injection mold includes a cavity portion for molding said cirrate members, said cavity portion being within a parting section acting as a mating portion for opening the mold and/or a parting section acting as a mating portion of the split mold;
injecting molten synthetic resin into said cavity portion while discharging gas present in the cavity portion to the outside by utilizing gaps in the parting section; and
molding said shaft member and cirrate members integrally.

16. An interdental cleaning tool manufacturing process for manufacturing an interdental cleaning tool according to claim 1, the process comprising steps of:
providing a split mold comprising a cavity for molding the shaft member and the cirrate members of the interdental cleaning tool;
wherein the split mold includes cavity portions for molding said cirrate members, said cavity portions being situated on a parting face thereof that intersects the axial direction of said shaft member;
injecting molten synthetic resin while parting faces of the mold of injection molding are mated; and
molding said shaft member and cirrate members integrally.

17. The interdental cleaning tool manufacturing process according to claim 16,
wherein said split mold has thickness of from 0.1 to 2 mm in an axial direction of the cavity for molding said shaft member thereof.

* * * * *